US010300007B2

(12) United States Patent
Hao et al.

(10) Patent No.: US 10,300,007 B2
(45) Date of Patent: May 28, 2019

(54) COMPOSITION COMPRISING OXIDATION DYE PRECURSORS AND ANIONIC POLYMERS

(71) Applicants: L'ORÉAL, Paris (FR); Yu Hao, Shanghai (CN); Xuekun Lv, Shanghai (CN)

(72) Inventors: Yu Hao, Shanghai (CN); Xuekun Lv, Shanghai (CN)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 14/655,268

(22) PCT Filed: Dec. 25, 2012

(86) PCT No.: PCT/CN2012/087414
§ 371 (c)(1),
(2) Date: Jun. 24, 2015

(87) PCT Pub. No.: WO2014/100971
PCT Pub. Date: Jul. 3, 2014

(65) Prior Publication Data
US 2015/0328128 A1 Nov. 19, 2015

(51) Int. Cl.
A61Q 5/10 (2006.01)
A61K 8/81 (2006.01)
A61K 8/41 (2006.01)
A61K 8/46 (2006.01)
A61K 8/86 (2006.01)

(52) U.S. Cl.
CPC ............ *A61K 8/8152* (2013.01); *A61K 8/411* (2013.01); *A61K 8/415* (2013.01); *A61K 8/463* (2013.01); *A61K 8/8147* (2013.01); *A61K 8/86* (2013.01); *A61Q 5/10* (2013.01); *A61K 2800/548* (2013.01); *A61K 2800/5424* (2013.01); *A61K 2800/594* (2013.01); *A61K 2800/88* (2013.01)

(58) Field of Classification Search
CPC ........ A61Q 5/10; A61K 8/463; A61K 8/8147; A61K 8/86; A61K 8/8152; A61K 8/415; A61K 8/411; A61K 2800/5424; A61K 2800/88; A61K 2800/594; A61K 8/548
USPC .......................................................... 8/405
See application file for complete search history.

(56) References Cited

U.S. PATENT DOCUMENTS

| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,766,576 A | 6/1998 | Löwe et al. |
| 6,099,592 A | 8/2000 | Vidal et al. |
| 6,284,003 B1 | 9/2001 | Rose et al. |
| 6,730,789 B1 | 5/2004 | Birault et al. |
| 7,070,769 B2 | 7/2006 | Ascione et al. |
| 2003/0056303 A1* | 3/2003 | Lim ........... A61K 8/347 8/405 |
| 2004/0055094 A1* | 3/2004 | Massoni ........... A61K 8/416 8/405 |
| 2006/0117493 A1* | 6/2006 | Bureiko ........... A61K 8/19 8/405 |
| 2009/0074692 A1 | 3/2009 | Biganska et al. |
| 2011/0311465 A1* | 12/2011 | Burg ........... A61K 8/8152 424/62 |
| 2012/0285479 A1* | 11/2012 | Zirwen ........... A61K 8/046 132/208 |
| 2012/0317734 A1* | 12/2012 | Martinez-Santiago ........... A61Q 5/10 8/416 |

FOREIGN PATENT DOCUMENTS

| CN | 1491100 A | 4/2004 |
| DE | 2359399 A1 | 6/1975 |
| DE | 3843892 A1 | 6/1990 |
| DE | 4133957 A1 | 4/1993 |
| DE | 19543988 A1 | 5/1997 |
| EP | 0770375 A1 | 5/1997 |
| FR | 2733749 A1 | 11/1996 |
| FR | 2801308 A1 | 5/2001 |
| FR | 2886136 A1 | 12/2006 |
| GB | 1026978 | 4/1966 |
| GB | 1153196 | 5/1969 |
| WO | 9408969 A1 | 4/1994 |
| WO | 9408970 A1 | 4/1994 |
| WO | 9615765 A1 | 5/1996 |
| WO | 2006060569 A2 | 6/2006 |
| WO | 2011146282 A2 | 11/2011 |

OTHER PUBLICATIONS

STIC Search Report dated Apr. 19, 2016.*
International Search Report dated Sep. 26, 2013, in PCT/CN2012/087414, 5 pages.
Written Opinion dated Sep. 26, 2013, in PCT/CN2012/087414, 4 pages.
International Preliminary Report on Patentability dated Jun. 30, 2015, in PCT/CN2012/087414, 5 pages.

* cited by examiner

*Primary Examiner* — Eisa B Elhilo
(74) *Attorney, Agent, or Firm* — Stinson Leonard Street LLP

(57) ABSTRACT

The present invention relates to a composition for dyeing keratin fibers, comprising a) at least one oxidation dye precursor, b) at least one anionic associative polymer i), c) at least one anionic non associative polymer ii), and d) at least one anionic surfactant. The composition optionally contains alkaline agent.

19 Claims, No Drawings

COMPOSITION COMPRISING OXIDATION DYE PRECURSORS AND ANIONIC POLYMERS

REFERENCE TO RELATED APPLICATIONS

This application is the 371 National Stage Application based on International Application Serial No. PCT/CN2012/087414, filed Dec. 25, 2012, the entire contents of which is incorporated herein by reference.

FIELD OF THE INVENTION

The present invention relates to a dyeing keratin fibers composition, more specifically, it refers to a hair dyeing composition comprising oxidation dye precursors, anionic polymers and anionic surfactant.

BACKGROUND OF THE INVENTION

It is known practice to dye keratin fibres, and in particular human hair, with dye compositions containing oxidation dye precursors, which are generally known as "oxidation bases", in particular ortho- or para-phenylenediamines, ortho- or para-aminophenols and heterocyclic bases.

Oxidation dye precursors are compounds that are initially uncoloured or sparingly coloured, which develop their dyeing power on the hair in the presence of oxidizing agents, leading to the formation of coloured compounds. The formation of these coloured compounds results either from an oxidative condensation of the "oxidation bases" with themselves, or from an oxidative condensation of the "oxidation bases" with coloration-modifying compounds, or "couplers", which are generally present in the dye compositions used in oxidation dyeing and are represented more particularly by meta-phenylenediamines, meta-aminophenols, meta-diphenols and certain heterocyclic compounds.

The variety of molecules used, consisting on the one hand of the "oxidation bases" and on the other hand of the "couplers", allows a very rich palette of colours to be obtained.

To localize the coloration product to application to the hair, so that it does not run onto the face or beyond the areas that are intended to be dyed, use has been made hitherto of conventional thickeners such as crosslinked polyacrylic acid, hydroxyethylcelluloses, waxes or alternatively mixtures of nonionic surfactants with a HLB (hydrophilic-lipophilic balance) that, when suitably selected, give rise to the gelling effect when they are diluted using water and/or surfactants.

It is also known that using anionic amphiphilic polymers in combination with oxidation dye precursor and oxidizing agent can obtain the hair dye compositions which do not run and thus remain better localized at the point of application.

However, the thickening systems mentioned above do not make it possible to obtain strong and chromatic shades with low selectivity and good fastness while at the same time ensuring good cosmetic condition of the treated hair. Moreover, the ready-to-use dye compositions containing oxidation dye precursor and also the thickening systems of the prior art do not allow a sufficiently precise application without running or drops in viscosity over time.

In some cases, the dyeing composition containing conventional thickeners along with the oxidation dye precursors exhibits before mixing with the oxidizing agents, a high viscosity. When mixed with the oxidizing agents, a homogeneous ready-to-use composition is difficult to obtain.

The aim of the invention is to provide a dyeing composition that does not run onto the face or out of the application area without impairing cosmetic and dyeing properties such as color intensity, selectivity and fastness with respect to chemical agents (shampooing, permanent-waving, etc.) or natural agents (light, perspiration, etc.), while at the same time giving the hair good cosmetic properties.

One of the aims of the present invention is to obtain a composition for dyeing the keratin fibers, especially the hair, with a low viscosity, however once mixing with a composition comprising oxidizing agent, the viscosity of the mixture immediately becomes sufficiently high for the mixture to be well localized on the hair, and at the same time conserving the dyeing properties obtained on the hair.

SUMMARY OF THE INVENTION

The aim of the present invention is achieved by a composition for dyeing keratin fibers, comprising a) at least one oxidation dye precursor, b) at least one anionic associative polymer i), c) at least one anionic non associative polymer ii), and d) at least one anionic surfactant. The composition optionally contains alkaline agent.

In another aspect, the present invention also relates to a two-compartment device, containing, in one compartment, a composition comprising at least one oxidation dye precursor, at least one anionic associative polymer i), at least one anionic non associative polymer ii), and at least one anionic surfactant, optionally at least one alkaline agent, and, in the other compartment, a composition comprising at least one oxidizing agent.

The present invention relates to a process for dyeing the keratin fibers, especially the hair, comprising applying on said keratin fibers the composition of the present invention.

According to one embodiment, a process for dyeing the keratin fibers, especially the hair, comprising mixing a composition free of oxidizing agent, comprising at least an oxidation dye precursor, at least one anionic associative polymer i), at least one anionic non associative polymer ii), and at least one anionic surfactant, optionally at least one alkaline agent, with a composition comprising at least one oxidizing agent, applying this composition to wet or dry human keratin fibers for a time sufficient to develop the desired coloration, and then rinsing the keratin fibers.

In other aspects, the invention also relates to the use of the composition of the invention for dyeing keratin fibers, in particular human keratin fibers such as hair.

Thus, the invention makes it possible to obtain a dyeing composition with low viscosity which is stable over time, and once mixed with oxidizing agents, become a homogeneous mixture with high viscosity which is sufficient for the mixture to remain in place after application on the hair, without risk of running At the same time, the composition of the invention gives on keratin fibers such as hair, excellent dyeing properties such as color intensity, selectivity and fastness as mentioned herein before.

In the description, the terms "at least a" or "at least one" are equivalent to "one or more".

Preferably, the keratin fibers according to the present invention are human keratin fibers, preferably the hair.

Other characteristics and advantages of the invention will emerge more clearly on reading the description and the examples that follow.

DETAILED DESCRIPTION OF THE INVENTION

The present invention relates to a composition for dyeing the keratin fibers, comprising a) at least one oxidation dye precursor, b) at least one anionic associative polymer i), c) at least one anionic non associative polymer ii), and d) at least one anionic surfactant. The composition optionally contains alkaline agent.

Oxidation Dye Precursors

As indicated previously, the composition according to the present invention comprises at least an oxidation dye precursor. Oxidation dye precursors may be selected from oxidation bases and couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred. Even more preferably mention may be made of para-phenylenediamine.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases, mention may be made, by way of example, of pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases of use in the present invention are the 3-aminopyrazolo[1,5-a]pyridine oxidation bases or the addition salts thereof described, for example, in Patent Application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and addition salts thereof.

Among the pyrimidine derivatives that may be mentioned are the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof, and tautomeric forms thereof, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4- methylaminopyrazole, 3,5-diamino-4-(β-hydroxyethyl) amino-1-methylpyrazole, and the addition salts thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a] pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl) amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or a salt thereof will preferably be used.

As heterocyclic bases, use will preferably be made of 4,5-diamino-1-(β-hydroxyethyl)pyrazole and/or 2,3-diamino-6,7-dihydro-1H,5H-pyrazolo[1,2-a]pyrazol-1-one and/or a salt thereof.

More specifically the oxidation bases are chosen from paraphenylenediamines and para-aminophenols, preferably para-phenylenediamine and/or para-aminophenol.

Among the couplers that may be used in the composition of the invention, mention may be made especially of meta-phenylenediamines, meta-aminophenols, meta-diphenols, naphthalene-based couplers and heterocyclic couplers, and also the addition salts thereof with an acid, and mixtures thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-1)]-1,2,4-triazole, 2,6-dimethyl[3,2-c]-1,2,4-triazole and 6-methylpyrazolo[1,5-a] benzimidazole, the addition salts thereof with an acid, and mixtures thereof.

More specifically, composition of the invention contains couplers chosen from meta-penylenediamines, meta-aminophenols such as 2,4-diaminophenoxyethanol, 4-amino-2-hydroxytoluene, 2-methyl-5-hydroxyethylaminophenol, and a mixture thereof.

The addition salts of the oxidation bases and couplers are especially chosen from the addition salts with an acid such as the hydrochlorides, hydrobromides, sulfates, citrates, succinates, tartrates, lactates, tosylates, benzenesulfonates, phosphates and acetates.

According to one embodiment, the oxidation dye precursors are selected from para-phenylenediamine, para-aminophenol, m-aminophenol, 2,4-diaminophenoxyethanol, 4-amino-2-hydroxytoluene, 2-methyl-5-hydroxyethylaminophenol, and a mixture thereof.

The oxidation base(s) are each generally present in an amount of from 0.0001% to 10% by weight relative to the total weight of the composition, and preferably from 0.005% to 7% by weight, more preferably from 0.1% to 4% by weight relative to the total weight of the composition.

The coupler(s) each generally represent from 0.0001% to 10% by weight relative to the total weight of the composition, and preferably from 0.005% to 7% by weight, more preferably from 0.1% to 4% by weight relative to the total weight of the composition.

Anionic Associative Polymer i)

Associative polymers are water-soluble polymers capable, in an aqueous medium, of reversibly associating together or with other molecules.

Their chemical structure comprises hydrophilic zones and hydrophobic zones characterized by at least one fatty chain.

The anionic associative polymer i) of the present invention preferably comes from the copolymerization between 1) and 2):
1) at least one ethylenically unsaturated mono or dicarboxylic acid monomer substituted by at least one, linear or branched, $(C_1-C_{10})$alkyl group; and
2) at least one associative monomer which is an ester of formula (I):

$$A\text{-}O\text{-}(Alk\text{-}O)_z\text{—}(CH_2)_w\text{—}R^a \quad (I)$$

Formula (I) wherein:

A represents a ethylenically unsaturated acyclic residue, optionally containing an additional carboxylic group or it salt, wherein said additional carboxylic group may be esterified with a linear or branched $(C_1-C_{20})$alkyl group;

$R^a$ represents an alkyl a linear or branched $(C_1-C_{30})$alkyl group, alkylaryl or arylalkyl group having from 1 to 30 carbon atoms wherein the alkyl group is linear or branched, preferably $R^a$ represents $(C_1-C_{20})$alkyl group, alkylphenyl or phenylakyl group having from 1 to 20 carbon atoms wherein the alkyl group is linear or branched;

Alk represents a linear or branched $(C_1-C_6)$alkylene group, particularly Alk represents —$CH_2$—$CH(R^b)$— wherein $R^b$ represents a hydrogen atom, or a $(C_1-C_4)$alkyl group such as methyl or ethyl group;

z is an integer comprised inclusively between 0 and 50;

w is an integer comprised inclusively between 0 and 30;

with the proviso that (I) contains at least one carboxyl group $C(O)OH$, or $C(O)O\text{-}Q^+$ wherein $Q^+$ represents cation chosen from an alkali metal, an alkaline earth metal, or ammonium.;

By polymerization of 1) and 2), it must be understood a copolymerization between at least one monomer 1) with at least one monomer 2).

According to an embodiment of the invention the copolymer comes from the polymerization between at least one ethylenically unsaturated mono or dicarboxylic acid monomer (1a) and at least one associative monomer which is an ester of formula (I) as defined herein before or (2a):

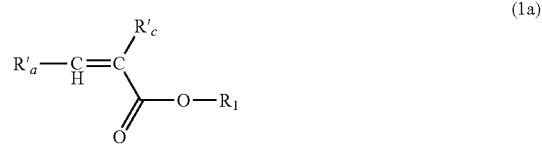

(1a)

-continued

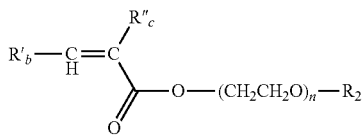
(2a)

Formulas (1a) and (2a) wherein:

R'$_a$ and R'$_b$, identical or different, represent a hydrogen atom, or a linear or branched (C$_1$-C$_6$)alkyl group, preferably R'$_a$ and R'$_b$ represent hydrogen atom;

R'$_c$ and R"$_c$, identical or different, represent a hydrogen atom, or a linear or branched (C$_1$-C$_6$)alkyl group, a C(O)OX group, or a -alk-C(O)OX group wherein X represents a hydrogen atom, an alkali metal, alkaline earth metal, or ammonium and -alk- represents a (C$_1$-C$_6$)alkylene group such as methylene group, preferably R'$_c$ and/or R"$_c$ represent a hydrogen atom or a methyl group;

R$_1$ represents a hydrogen atom, an alkali metal, alkaline earth metal, or a (C$_1$-C$_6$)alkyl group;

R$_2$ represents a, linear or branched, (C$_6$-C$_{40}$)alkyl group, preferably a (C$_{10}$-C$_{30}$)alkyl group;

n is an integer comprised inclusively between 5 and 100, particularly between 10 and 50, more particularly between 20 and 40, preferably between 20 and 30 such as 25;

with the proviso that (1a) or (2a) contain at least one carboxyl group C(O)OH, or C(O)O-Q$^+$ wherein Q$^+$ represents cation chosen from an alkali metal, alkaline earth metal or ammonium.;

Particularly R'$_a$, R'$_b$ represent a hydrogen atom and R'$_c$, and R"$_c$ represent a hydrogen atom or a methyl group and R$_1$ represents a hydrogen atom, an alkali metal, alkaline earth metal.

According to another variant R'$_a$, R'$_b$, and R'$_c$, represent a hydrogen atom and R"$_c$ represents a group -alk-C(O)OX such as —CH2-C(O)OX wherein X is as defined herein before.

According to a particular embodiment of the invention, the polymer i) contains units (Ia) and/or (I'a):

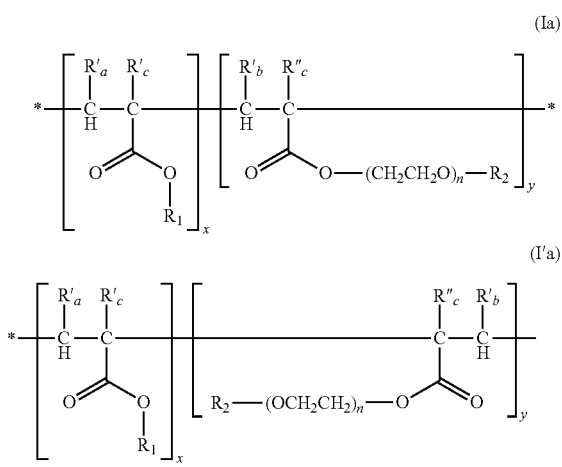

wherein

R'$_a$, R'$_b$, R'$_c$, R"$_c$ are as defined herein before;

x represents an integer, preferably more than 100, more preferably between 100 and 10000;

y represents an integer, preferably more than 100, more preferably between 100 and 10000;

and x+y represents an integer, preferably>200, more preferably between 200 and 20000.

According to a preferred embodiment, the anionic associative polymer i) of the present invention has a molecular weight of more than 100000, preferably between 200000 and 8000000.

According to a preferred embodiment, in formula (Ia) and (I'a), R$_1$ represents a hydrogen atom, an alkali metal, or an alkaline earth metal.

As example of copolymer (1a)/(2a) as defined herein before, usable in the invention, we may mention: acrylates/palmeth-25 acrylate copolymer, such as the products commercially available from 3V under the trade name Synthalen® W2000, acrylates/beheneth-25 methacrylate copolymer, such as the products commercially available from Lubrizol under the trade name Novethix® L-10, acrylates/steareth-20 methacrylate copolymer, such as the products commercially available from Rohm and Haas (Dow Chemical) under the trade name Aculyn™ 22 polymer, acrylates/steareth-20 itaconate copolymer, such as the products commercially available from AkzoNobel under the trade name Structure 2001, acrylates/ceteth-20 itaconate copolymer, such as the products commercially available from AkzoNobel under the trade name Structure 3001, acrylates/ceteth-20 methacrylate copolymer, acrylate/beheneth-25 itaconate copolymer, acrylate/palmeth-25 methacrylates copolymer, acrylate/steareth-50 acrylate copolymer, acrylates/palmeth-25 itaconate copolymer, such as the products commercially available from Sigma-3V under the trade name Polygel W 40, and mixtures thereof.

Among the above said polymers, the products sold by the company 3V Group under the tradename Synthalen® W2000 is specially preferred.

The anionic associative polymer i) described above are preferably used according to the invention in an amount which may range from 0.3 to 2.5% by weight, preferably from 0.6 to 2.2% by weight, more preferably from 0.8 to 2.0% by weight, most preferably from 0.9 to 1.8% by weight relative to the total weight of the composition.

Anionic Non Associative Polymer ii)

The anionic non associative polymer ii) contains hydrophilic units of unsaturated olefinic carboxylic acid, and potentially in the presence of at least one cross-linking agent.

The anionic non associative polymer ii) is chosen from those obtained from at least one monomer of formula (3) below:

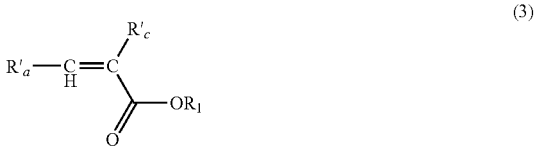
(3)

Formula (3) in which R'$_a$ and R'$_c$ and R$_1$ are as defined herein before, more specifically R'$_a$ represents a hydrogen atom, R'$_c$ represents a hydrogen atom, a methyl group or a ethyl group with the proviso that at least one monomer is such that R$_1$ represents a hydrogen atom, an alkali metal, alkaline earth metal. According to a particular embodiment, the polymer is a polymer obtained from monomer (3) as previously defined with R$_1$ represents a hydrogen atom, an alkali metal, alkaline earth metal.

According to another embodiment, the anionic non associative polymer is a homopolymer obtained from acrylic acid monomers or methacrylic acid monomers, preferably acrylic acid monomers.

According to the present invention, the anionic non associative polymer can be cross linked. By crosslinking agent it must be understood an agent able to make links between molecular chains to form a three-dimensional network of connected molecules (co) or (homo)polymers.

The said crosslinking agent is a monomer more specifically containing at least one group ethylenyl or allylether group as the following formula (4) or (5):

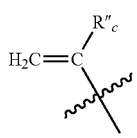

(4)

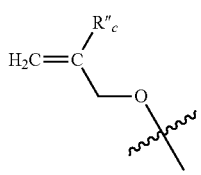

(5)

formula (4) or (5) wherein $R''_c$ is as defined herein before, more particularly represent H or methyl group, with at least one other polymerizable group whose unsaturated bonds are not conjugated to each other. Mentions may be made of derivatives of ethylene glycol di(meth)acrylate such as ethylene glycol diacrylate, di(ethylene glycol) diacrylate, tetra(ethylene glycol) diacrylate, ethylene glycol dimethacrylate, di(ethylene glycol) dimethacrylate, tri(ethylene glycol) dimethacrylate, derivatives of methylenebisacrylamide such as N,N-methylenebisacrylamide, N,N-methylenebisacrylamide, N,N-(1,2-dihydroxyethylene)bisacrylamide, formaldehyde-free crosslinking agent such as N-(1-hydroxy-2,2-dimethoxyethyl)acrylamide, and divinylbenzene, and (poly)allylether.

Preferably the monomers (3) are polymerized in a presence of cross-linking agent especially in a presence of (poly)allyl ethers in particular, (poly)allyl sucrose and (poly)allyl pentaerylthritol such as carbomer which correspond to a homopolymer of acrylic acid crosslinked with an allyl ether of pentaerythritol, an allyl ether of sucrose, or an allyl ether of propylene.

The anionic non associative polymer ii) can be selected Carbomer. Carbomer is a crosslinked homopolymer of acrylic. This Carbomer are for example sold under the trade name Carbopol® 940, Carbopol® 941, Carbopol® 980, Carbopol® 981, preferably Carbopol® 981.

The amount of anionic non associative polymers ii) may range from 0.001 to 2.5% by weight, preferably from 0.02 to 2.0% by weight, more preferably from 0.1 to 1.8% by weight, most preferably from 0.5 to 1.5% by weight relative to the total weight of the composition.

Anionic Surfactant

According to an embodiment of the invention the at least surfactant is chosen from the anionic surfactant (also called "surface-active agent").

Anionic surfactant agent is understood to mean an amphiphilic compound in which the hydrophobic part carries an anionic hydrophilic group with a cationic counterion which is generally metallic (alkali metal, such as Na or K) or ammonium; the hydrophilic group is thus polar and capable of dissociating to give anions in aqueous solution.

More particularly the anionic part of the anionic surfactant is belonging to the group chosen from: $C(O)OH$, $—C(O)O^-$, $—SO_3H$, $—S(O)_2O^-$, $—OS(O)_2OH$, $—OS(O)_2^-$, $—P(O)OH_2$, $—P(O)_2O^-$, $—P(O)O_2—$, $—P(OH)_2$, $=P(O)OH$, $—P(OH)O^-$, $=P(O)O^-$, $=POH$, $=PO^-$, the anionic part comprizing a cationic counter anion such as alkali or alkaline earth metal or organic cationic counter anion such as ammonium. Mention may be made, as anionic surface-active agents, of surface-active agents comprising carboxylate, sulfate, sulfonate, sulfoacetate, sulfosuccinate, phosphate, isethionate, sarcosinate, glutamate, lactylate or taurate anionic groups, salts of fatty acids, salts of galactosiduronic acids, salts of ether carboxylic acids and their mixtures.

More particularly, the anionic surface-active agent or agents according to the invention are chosen from:

$(C_6-C_{30})$alkyl sulfates, $(C_6-C_{30})$alkyl ether sulfates, $(C_6-C_{30})$alkylamido ether sulfates, alkylaryl polyether sulfates or monoglyceride sulfates;

$(C_6-C_{30})$alkyl sulfonates, $(C_6-C_{30})$alkylamidesulfonates, $(C_6-C_{30})$alkylaryl sulfonates, α-olefin sulfonates, paraffin sulfonates;

$(C_6-C_{30})$akyl phosphates;

$(C_6-C_{30})$alkyl sulfosuccinates, $(C_6-C_{30})$alkyl ether sulfosuccinates or $(C_6-C_{30})$alkylamido sulfosuccinates;

$(C_6-C_{30})$alkyl sulfoacetates;

$(C_6-C_{24})$acylsarcosinates;

$(C_6-C_{24})$acylglutamates;

$(C_6-C_{30})$alkylpolyglycoside carboxylic ethers; $(C_6-C_{30})$alkylpolyglycoside sulfosuccinates;

$(C_6-C_{30})$alkyl sulfosuccinamates;

$(C_6-C_{24})$acyl isethionates;

N-[$(C_6-C_{24})$acyl]taurates;

salts of fatty acids;

$C_8-C_{20}$)acyl lactylates;

salts of $(C_6-C_{30})$alkyl-D-galactosiduronic acids;

salts of $(C_6-C_{30})$alkyl polyoxyalkylenated ether carboxylic acids, of $(C_6-C_{30})$alkylaryl polyoxyalkylenated ether carboxylic acids or of $(C_6-C_{30})$alkylamido polyoxyalkylenated ether carboxylic acids;

and their mixtures.

These anionic surface-active agents are advantageously found in the form of salts in the composition according to the invention, in particular of salts of alkali metals, such as sodium; of alkaline earth metals, such as, for example, magnesium; of ammonium salts; of amine salts; or of aminoalcohol salts. They might also, according to the conditions, occur in their acid form.

It should be noted that the alkyl or acyl radicals of these various compounds preferably comprise from 12 to 20 carbon atoms. Preferably, the aryl radical denotes a phenyl or benzyl group.

Furthermore, the polyoxyalkylenated anionic surface-active agents preferably comprise from 2 to 50 alkylene oxide groups, in particular ethylene oxide groups.

In accordance with a preferred embodiment of the invention, the anionic surface-active agent is chosen from salts of fatty acids or sulfates surfactant.

Preferably, the anionic surfactants of the invention are sulfates, more specifically are chosen from $(C_6-C_{30})$alkyl sulfates, $(C_6-C_{30})$alkyl ether sulfates, $(C_6-C_{30})$alkylamido ether sulfates, alkylaryl polyether sulfates and monoglyceride sulfates, their salts such as alkali salts, such as sodium, and their mixtures.

More preferably the anionic surfactants of the invention are chosen from ($C_6$-$C_{30}$)alkyl sulfates, ($C_6$-$C_{30}$)alkyl ether sulfates, particularly ($C_6$-$C_{30}$)alkyl ether sulfates such as lauryl ether sulfate, their salts, such as sodium laureth sulfate.

Advantageously, the content of anionic surface-active agent(s) represents from 0.1 to 7.5% by weight, preferably from 0.6 to 7.0% by weight, more preferably from 0.7% to 6.0% by weight, most preferably from 1.4% to 5.6% by weight relative to the total weight of the composition.

In one aspect, the current invention relates to a composition for dyeing the keratin fibers, comprising at least an oxidation dye precursor selected from para-phenylenediamine, para-aminophenol, m-aminophenol, 2,4-diaminophenoxyethanol, 4-amino-2-hydroxytoluene, 2-methyl-5-hydroxyethylaminophenol, and a mixture thereof; at least an anionic associative polymer i) selected from acrylates/palmeth-25 acrylate copolymer, acrylate/palmeth-25 methacrylates copolymer, acrylates/palmeth-25 itaconate copolymer, and a mixture thereof; at least an anionic non associative polymer ii) selected from acrylic homo-or copolymer; and at least an anionic surfactant selected from sodium laureth sulfate, sodium laureth sulfonate, sodium laureth phosphate, potassium laureth phosphate, and a mixture thereof.

Alkaline Agent

The composition further comprises at least an alkaline agent(s). This agent may be chosen from mineral or organic or hybrid alkaline agents, or mixtures thereof.

The mineral alkaline agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a pKb at 25° C. of less than 12, preferably less than 10 and even more advantageously less than 6. It should be noted that it is the pKb corresponding to the function of highest basicity.

Hybrid compounds that may be mentioned include the salts of the amines mentioned previously with acids such as carbonic acid or hydrochloric acid.

The organic alkaline agent(s) are chosen, for example, from alkanolamines, oxyethylenated and/or oxypropylenated ethylenediamines, amino acids and the compounds of formula below:

in which W is a $C_1$-$C_6$ alkylene residue optionally substituted with a hydroxyl group or a $C_1$-$C_6$ alkyl radical; $R_x$, $R_y$, $R_z$, and $R_t$, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for performing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane, preferably monoethanolamine.

The composition of the invention preferably contains one or more alkanolamines. More preferentially still, the organic amine is monoethanolamine.

In one variant of the invention, the composition of the invention further comprises as alkaline agent one or more alkanolamines (preferably monoethanolamine) and/or aqueous ammonia. In the variant where the alkaline agent is a combination of alkanolamine(s) and ammonia, the alkanolamines are present in predominant amount relative to the aqueous ammonia.

Advantageously, the composition according to the invention further has a content of alkaline agent(s) ranging from 0.01% to 30% by weight, preferably from 0.1% to 20% by weight and better still from 1% to 10% by weight, and even more preferably from 2% to 8% by weight relative to the weight of said composition.

Oxidizing Agent

The composition of the present invention further comprises at least an oxidizing agent.

The oxidizing agents are especially chemical oxidizing agent, in other word it is different from the oxygen of the air. Preferably the oxydizing agent is chosen, for example, from hydrogen peroxide, urea peroxide, alkali metal bromates or ferricyanides, peroxygenated salts, for instance persulfates, perborates, peracids, and precursors thereof and percarbonates of alkali metals or of alkaline-earth metals. Advantageously, the oxidizing agent is hydrogen peroxide.

The content of oxidizing agent(s) more particularly represents from 0.1% to 20% by weight and preferably from 0.5% to 10% by weight relative to the weight of the composition.

The composition according to the invention may also contain various adjuvants conventionally used in cosmetic compositions for dyeing keratin fibers in particular hair, such as cationic, nonionic, amphoteric or zwitterionic surfactants or mixtures thereof, cationic, nonionic, amphoteric or zwitterionic polymers, or blends thereof, mineral or organic thickeners, and in particular cationic, nonionic and amphoteric associative polymer thickeners, antioxidants, penetrating agents, sequestering agents, fragrances, buffers, dispersing agents, conditioning agents such as, for example, modified or unmodified, volatile or non-volatile silicones, such as amino silicones, film-forming agents, ceramides, preservatives, opacifiers or conductive polymers.

The above adjuvants are generally present in an amount for each of them of between 0.01% and 20% by weight relative to the weight of the composition.

The composition according to the invention is presented for application to keratin fibers in the form of gel, or cream, preferably gel.

The present invention also relates to a two-compartment device containing, in one compartment, a composition, as described above, comprising at least one oxidation dye precursor, at least one anionic associative polymer, at least one anionic non associative polymer, and at least one anionic surfactant, optionally at least one alkaline agent, and, in the other compartment, a composition comprising at least one oxidizing agent.

A process for dyeing the keratin fibers, especially the hair, thus comprising applying on the said keratin fibers the composition according to the present invention.

According to one embodiment, a process for dyeing the keratin fibers, especially the hair, comprising mixing a composition free of oxidizing agent, comprising at least one oxidation dye precursor, at least one anionic associative polymer, at least one anionic non associative polymer, and at least one anionic surfactant, optionally at least one alkaline agent, with a composition comprising at least an oxidizing agent, and applying this composition to wet or dry human keratin fibers.

The composition is then left in place for a time usually ranging from 1 minute to 1 hour and preferably from 5 minutes to 30 minutes, more preferably from 5 minutes to 20 minutes.

The temperature during the process is conventionally between room temperature, 15° C. and 25° C. and 80° C., preferably between room temperature and 60° C.

After the treatment, the human keratin fibers are optionally rinsed with water, optionally washed with a shampoo and then rinsed with water, before being dried or left to dry.

EXAMPLES

The following compositions Invention A, B, and C were prepared, as shown in Table 1:

TABLE 1

| INCI Name | % by weight of the active ingredient | | |
|---|---|---|---|
| | Invention A | Invention B | Invention C |
| Ethanolamine (Amino-2-ethanol, Monoethanolamine Care from BASF) | 4.72 | 4.72 | 4.72 |
| 2,4-Diaminophenoxyethanol HCl (2,4-Diaminophenoxyethanol HCl, 24Dape Lo-Bleu from Dragon Chemical) | 0.8 | 0.8 | 0.8 |

TABLE 1-continued

| INCI Name | % by weight of the active ingredient | | |
|---|---|---|---|
| | Invention A | Invention B | Invention C |
| Resorcinol (Resorcinol, Resorcinol Technical Grade Flake from Indspec Chemical Corporation) | 2 | 2 | 2 |
| m-Aminophenol (m-Aminophenol, Rodol EG from Lowenstein) | 0.3 | 0.3 | 0.3 |
| p-Phenylenediamine (para-phenylenediamine, PPDA 99.5% OR from Chemstar) | 2.2 | 2.2 | 2.2 |
| Carbomer (polyacrylic acid, Carbopol ® 981 Polymer from Lubrizol) | 0.05 | 0.7 | 2.0 |
| Acrylates/Palmeth-25 acrylate copolymer (Synthalen ® W2000 from 3V) | 1.5 | 2.1 | 0.6 |
| Sodium laureth sulfate 70% containing 1 mol of ethylene oxide (Sodium laureth sulfate, SLES(N1EO) from Zhejiang Zanyu Technology) | 0.5 | 4.0 | 5.6 |
| Water | Up to 100 | Up to 100 | Up to 100 |

Invention A, B and C are stable over time. Each of them was mixed with same amount comparing to its own weight of an oxidizing composition comprising 6% hydrogen peroxide at pH 2.

During the mixing process, the viscosity of the composition changed immediately from low viscosity to high viscosity, which on one hand, makes it easy to obtain a homogeneity mixture, and on the other hand, makes it easy to apply the composition to the hair without risks of running After a leave-on time of 10 minutes at 25° C. following by rinsing, the hair is washed and dried. The head of hair is then uniformly dyed in an intense black colour with the mixtures obtained from compositions Invention A, B and C.

The following compositions Comparative A, B, and C were prepared, as shown in Table 2:

TABLE 2

| INCI Name | % by weight of the active ingredient | | |
|---|---|---|---|
| | Comparative A | Comparative B | Comparative C |
| Ethanolamine (Amino-2-ethanol, Monoethanolamine Care from BASF) | 4.72 | 4.72 | 4.72 |
| 2,4-Diaminophenoxyethanol HCl (2,4-Diaminophenoxyethanol HCl, 24Dape Lo-Bleu from Dragon Chemical) | 0.8 | 0.8 | 0.8 |
| Resorcinol (Resorcinol, Resorcinol Technical Grade Flake from Indspec Chemical Corporation) | 2 | 2 | 2 |
| m-Aminophenol (m-Aminophenol, Rodol EG from Lowenstein) | 0.3 | 0.3 | 0.3 |
| p-Phenylenediamine (para-phenylenediamine, PPDA 99.5% OR from Chemstar) | 2.2 | 2.2 | 2.2 |
| Carbomer (polyacrylic acid, Carbopol ® 981 Polymer from Lubrizol) | 2 | 3 | 0 |
| Acrylates/Palmeth-25 acrylate copolymer (Synthalen ® W2000 from 3V) | 0 | 4 | 2 |

TABLE 2-continued

| | % by weight of the active ingredient | | |
|---|---|---|---|
| INCI Name | Comparative A | Comparative B | Comparative C |
| Sodium laureth sulfate 70% containing 1 mol of ethylene oxide (Sodium laureth sulfate, SLES(N1EO) from Zhejiang Zanyu Technology) | 0 | 0 | 6 |
| Water | Up to 100 | Up to 100 | Up to 100 |
| Effect | Not stable in the presence of oxidation dye precursor | Not applicable due to the high viscosity before mixing with $H_2O_2$, and not easy to spread on the hair after mixing with $H_2O_2$ | Viscosity is too low before and after mixing with $H_2O_2$, moreover foam appears in the composition |

Each composition of Inventions A, B, C, and Comparative A, B, and C was mixed with same amount comparing to its own weight of an oxidizing composition comprising 6% hydrogen peroxide at pH 2. The compositions and the mixtures after mixing with hydrogen peroxide are evaluated by a panel of 6 hair dressers in terms of immediate change in viscosity, the dyeing properties such as color intensity, selectivity and fastness, according to the method mentioned herein before.

Based on the investigation, the compositions of invention A, B, and C have porper, low viscosity before mixing with $H_2O_2$, and immediately become sufficiently high viscous after mixing with $H_2O_2$. The mixtures obtained by mixing compositions of A, B, and C with $H_2O_2$ is homogeneous, with comparison to the compositions of Comparative A, B, and C, wherein Comparative A is not stable in the presence of oxidation dye precursor, Comparative B is too viscous before and after mixing with $H_2O_2$, and Comparative C is too liquid before and after mixing with $H_2O_2$, which makes it difficult to apply on the hair.

In terms of dyeing properties, the experts found that the hair using the Invention A, B, and C, with comparison to the hair using Comparative A, B, and C, bring to the hair significantly better and intensive color, and less selectivity between the root and tip of the hair. Moreover, it is much time-saving during application, when using the examples of Invention A, B, and C, as comparing to the Comparative A, B, and C.

Application Performance Tests:

Application performance of the compositions with different concentrations of the active ingredients are tested by 5 hair dressers by giving scores to the easiness of mixing with the oxidizing composition, and applying on hair. For each score, 5 stands for the best performance, i.e. obtaining a homogeneity mixture, and easy to apply the composition to the hair without risks of running, whereas 1 stands for the worst performance.

Test example 1: Compositions comprising Acrylates/Palmeth-25 methacrylates copolymer with different concentrations The following compositions were prepared, as shown in Table 3:

TABLE 3

| | | % by weight of the raw material | | |
|---|---|---|---|---|
| INCI Name | | Comparative 1 | Invention 1 | Invention 2 |
| Ethanolamine (Amino-2-ethanol, Monoethanolamine Care from BASF) | | 4.72 | 4.72 | 4.72 |
| 2,4-Diaminophenoxyethanol HCl (2,4-Diaminophenoxyethanol HCl, 24Dape Lo-Bleu from Dragon Chemical) | | 0.8 | 0.8 | 0.8 |
| Resorcinol (Resorcinol, Resorcinol Technical Grade Flake from Indspec Chemical Corporation) | | 2 | 2 | 2 |
| m-Aminophenol (m-Aminophenol, Rodol EG from Lowenstein) | | 0.3 | 0.3 | 0.3 |
| p-Phenylenediamine (para-phenylenediamine, PPDA 99.5% OR from Chemstar) | | 2.2 | 2.2 | 2.2 |
| Carbomer (polyacrylic acid, Carbopol ® 981 Polymer from Lubrizol) | | 0.2 | 0.2 | 0.2 |
| Acrylates/Palmeth-25 acrylate copolymer (Synthalen ® W2000 from 3V) | | 0 | 0.9 | 1.8 |
| Sodium laureth sulfate 70% containing 1 mol of ethylene oxide (Sodium laureth sulfate, SLES(N1EO) from Zhejiang Zanyu Technology) | | 1.4 | 1.4 | 1.4 |
| Water | | Up to 100 | Up to 100 | Up to 100 |
| Application performance | Mixing with the oxidizing composition | 5 | 5 | 3 |
| | Applying on hair | 1 | 5 | 5 |

As shown in the Table 3, the composition of Inventions 1 and 2 are much better in terms of application performances, in comparison with Comparative 1.

Test example 2: Compositions comprising Sodium laureth sulfate with different concentrations The following compositions were prepared, as shown in Table 4:

TABLE 4

| INCI Name | % by weight of the raw material | | |
|---|---|---|---|
| | Comparative 2 | Invention 3 | Invention 4 |
| Ethanolamine (Amino-2-ethanol, Monoethanolamine Care from BASF) | 4.72 | 4.72 | 4.72 |
| 2,4-Diaminophenoxyethanol HCl (2,4-Diaminophenoxyethanol HCl, 24Dape Lo-Bleu from Dragon Chemical) | 0.8 | 0.8 | 0.8 |
| Resorcinol (Resorcinol, Resorcinol Technical Grade Flake from Indspec Chemical Corporation) | 2 | 2 | 2 |
| m-Aminophenol (m-Aminophenol, Rodol EG from Lowenstein) | 0.3 | 0.3 | 0.3 |
| p-Phenylenediamine (para-phenylenediamine, PPDA 99.5% OR from Chemstar) | 2.2 | 2.2 | 2.2 |
| Carbomer (polyacrylic acid, Carbopol ® 981 Polymer from Lubrizol) | 0.2 | 0.2 | 0.2 |
| Acrylates/Palmeth-25 acrylate copolymer (Synthalen ® W2000 from 3V) | 1.5 | 1.5 | 1.5 |
| Sodium laureth sulfate 70% containing 1 mol of ethylene oxide (Sodium laureth sulfate, SLES(N1EO) from Zhejiang Zanyu Technology) | 0 | 2.8 | 5.6 |
| Water | Up to 100 | Up to 100 | Up to 100 |
| Application performance — Mixing with the oxidizing composition | 3 | 5 | 5 |
| Applying on hair | 2 | 5 | 5 |

As shown in the Table 4, the composition of Inventions 3 and 4 are much better in terms of application performances, in comparison with Comparative 2.

Test example 3: Compositions comprising polyacrylic acid with different concentrations The following compositions were prepared, as shown in Table 5:

TABLE 5

| INCI Name | % by weight of the raw material | | |
|---|---|---|---|
| | Comparative 3 | Invention 5 | Invention 6 |
| Ethanolamine (Amino-2-ethanol, Monoethanolamine Care from BASF) | 4.72 | 4.72 | 4.72 |
| 2,4-Diaminophenoxyethanol HCl (2,4-Diaminophenoxyethanol HCl, 24Dape Lo-Bleu from Dragon Chemical) | 0.8 | 0.8 | 0.8 |
| Resorcinol (Resorcinol, Resorcinol Technical Grade Flake from Indspec Chemical Corporation) | 2 | 2 | 2 |
| m-Aminophenol (m-Aminophenol, Rodol EG from Lowenstein) | 0.3 | 0.3 | 0.3 |
| p-Phenylenediamine (para-phenylenediamine, PPDA 99.5% OR from Chemstar) | 2.2 | 2.2 | 2.2 |
| Carbomer (polyacrylic acid, Carbopol ® 981 Polymer from Lubrizol) | 0 | 0.75 | 1.5 |
| Acrylates/Palmeth-25 acrylate copolymer (Synthalen ® W2000 from 3V) | 1.5 | 1.5 | 1.5 |
| Sodium laureth sulfate 70% containing 1 mol of ethylene oxide (Sodium laureth sulfate, SLES(N1EO) from Zhejiang Zanyu Technology) | 0.7 | 0.7 | 0.7 |
| Water | Up to 100 | Up to 100 | Up to 100 |
| Application performance — Mixing with the oxidizing composition | 3 | 5 | 5 |
| Applying on hair | 2 | 5 | 5 |

As shown in the Table 5, the composition of Inventions 5 and 6 are much better in terms of application performances, in comparison with Comparative 3.

The invention claimed is:

1. A composition for dyeing keratin fibers, the composition in the form of a gel or cream and comprising:
   a) at least one oxidation dye precursor;
   b) at least one anionic associative polymer selected from the group consisting of acrylates/palmeth-25 acrylate copolymer, acrylate/palmeth-25 methacrylate copolymer, and mixtures thereof;
   c) at least one anionic non associative polymer chosen from those obtained from at least one monomer of formula (3) below:

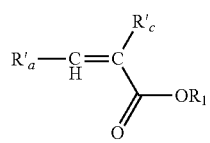

(3)

wherein:
R'$_a$ represents a hydrogen atom or a linear or branched (C$_1$-C$_6$)alkyl group;
R'$_c$ represents a hydrogen atom, a linear or branched (C$_1$-C$_6$)alkyl group, a C(O)OX group, or a -alk-C(O)OX group, wherein X represents a hydrogen atom, an alkali metal, alkaline earth metal, or ammonium and -alk- represents a (C$_1$-C$_6$)alkylene group;
and R$_1$ represents a hydrogen atom, an alkali metal, an alkaline metal, or a (C$_1$-C$_6$)alkyl group;
   d) at least one anionic surfactant;
   e) at least one alkaline agent comprising an alkanolamine, and
   f) at least one oxidizing agent.

2. The composition according to claim 1, wherein the oxidation dye precursor is selected from oxidation bases and couplers.

3. The composition according to claim 2, wherein the oxidation bases are selected from para-phenylenediamines, bis(phenyl)alkylenediamines, para-aminophenols, ortho-aminophenols, heterocyclic bases, their salts of organic or inorganic acid, their optical or geometric isomers, tautomers and solvates, and a mixture thereof, and the couplers are selected from meta-aminophenols, meta-phenylenediamines and meta-diphenols, naphthols, mono- or polyhydroxylated naphthalene derivatives, heterocyclic couplers, their salts of organic or inorganic acid, their optical or geometric isomers, tautomers, solvates, and a mixture thereof.

4. The composition according to claim 1, wherein the at least one oxidation dye precursor is selected from the group consisting of para-phenylenediamine, meta-aminophenol, para-aminophenol and meta-diphenol, their salts of organic or inorganic acid, solvates, and a mixture thereof.

5. The composition according to claim 1, wherein the at least one anionic non associative polymer further contains at least one cross-linking agent, wherein the crosslinking agent is a monomer containing at least one ethylenyl or allylether group of formula (4) or (5):

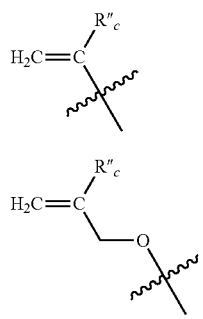

wherein:
R"$_c$, represents a hydrogen atom, a linear or branched ($C_1$-$C_6$)alkyl group, a C(O)OX group, or a -alk-C(O)OX group, wherein X represents a hydrogen atom, an alkali metal, an alkaline earth metal, or ammonium, and -alk- represents a ($C_1$-$C_6$)alkylene group,
with at least one other polymerizable group whose unsaturated bonds are not conjugated to each other.

6. The composition according to claim 5, wherein the cross-linking agent is selected from the group consisting of derivatives of ethylene glycol di(meth)acrylate, derivatives of methylenebisacrylamide, formaldehyde-free crosslinking agents, (poly)allylethers, or a mixture thereof.

7. The composition according to claim 5, wherein the anionic non associative polymer is obtained by polymerization of monomers of formula (3) in the presence of at least one cross-linking agent.

8. The composition according to claim 1, wherein the at least one anionic non associative polymer is polyacrylic acid.

9. The composition according to claim 1, wherein the at least one anionic surfactant is a sulfate surfactant.

10. The composition according to claim 1, wherein the at least one anionic surfactant is chosen from ($C_6$-$C_{30}$)alkyl sulfates, ($C_6$-$C_{30}$)alkyl ether sulfates ($C_6$-$C_{30}$)alkylamido ether sulfates, alkylaryl polyether sulfates, monoglyceride sulfates, and a mixture thereof.

11. The composition according to claim 1, comprising from 0.3 to 2.5% by weight of the at least one anionic associative polymer, based on the total weight of the composition.

12. The composition according to claim 1, comprising from 0.001 to 2.5% by weight of the at least one anionic non associative polymer, or a mixture thereof, based on the total weight of the composition.

13. The composition according to claim 1, comprising from 0.1 to 7.5% by weight of the at least one anionic surfactant, based on the total weight of the composition.

14. A two-compartment device containing, in one compartment, a composition according to claim 1, and, in the other compartment, a composition comprising at least one oxidizing agent.

15. A process for dyeing keratin fibers wherein the composition according to claim 1 is applied on the keratin fibers.

16. The composition according to claim 1, wherein the alkaline agent is selected from the group consisting of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and combinations thereof.

17. The composition of according to claim 16, wherein the alkaline agent is monoethanolamine.

18. The composition according to claim 1, wherein the alkaline agent has a pKb of less than 12 at a temperature of 25° C.

19. The composition according to claim 1, wherein the alkaline agent is from about 0.01 wt% to about 30 wt% relative to the weight of the composition.

* * * * *